United States Patent
Biedermann et al.

(10) Patent No.: US 9,895,173 B2
(45) Date of Patent: Feb. 20, 2018

(54) ELEMENT WITH A SHANK AND A HOLDING ELEMENT CONNECTED TO IT FOR CONNECTING TO A ROD

(71) Applicant: BIEDERMANN TECHNOLOGIES GMBH & CO. KG, Donaueschingen (DE)

(72) Inventors: Lutz Biedermann, VS-Villingen (DE); Jürgen Harms, Karlsruhe (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 15/094,784

(22) Filed: Apr. 8, 2016

(65) Prior Publication Data

US 2016/0220282 A1     Aug. 4, 2016

Related U.S. Application Data

(63) Continuation of application No. 14/327,434, filed on Jul. 9, 2014, which is a continuation of application (Continued)

(30) Foreign Application Priority Data

Nov. 27, 2001    (DE) .................................. 101 57 969

(51) Int. Cl.
*A61B 17/70* (2006.01)
*F16B 7/18* (2006.01)
(Continued)

(52) U.S. Cl.
CPC ...... *A61B 17/7037* (2013.01); *A61B 17/7032* (2013.01); *A61B 17/7035* (2013.01);
(Continued)

(58) Field of Classification Search
CPC ............ A61B 17/7032; A61B 17/7035; A61B 17/7037; F16B 33/02
See application file for complete search history.

(56) References Cited

U.S. PATENT DOCUMENTS

| 2,005,348 A | 6/1935 | Michell |
| 2,005,995 A | 6/1935 | Knox |

(Continued)

FOREIGN PATENT DOCUMENTS

| DE | 299 03 342 U1 | 7/1999 |
| DE | 298 10 798 U1 | 12/1999 |

(Continued)

OTHER PUBLICATIONS

Product information for Medtronic Sofamor Danek; CD Horizon Legacy 5.5 Spinal System dated 2003.

(Continued)

*Primary Examiner* — Anu Ramana
(74) *Attorney, Agent, or Firm* — Lewis Roca Rothgerber Christie LLP

(57) ABSTRACT

An element with a shank (1) and a holding element (2) connected to it for connecting to a rod (100) is provided, wherein the holding element (2) has a recess (3) having a U-shaped cross-section for receiving the rod (100) with two legs (4, 5) open at one end (6) and an inner thread (7) on the open legs (4, 5) and a locking element (9) with an outer thread (8) which cooperates with the inner thread of the legs, wherein the inner thread (7) of the legs and the outer thread (8) of the locking element are constructed with a flat thread in which the two flanks (7a, 7b; 8a, 8b)) enclose an angle of 90° in each case with the screw axis (S, M). This prevents splaying of the open legs when the locking element is screwed in. The flat thread is easy to produce.

35 Claims, 4 Drawing Sheets

Related U.S. Application Data

No. 10/306,057, filed on Nov. 27, 2002, now Pat. No. 8,828,060.

(51) Int. Cl.
*F16B 33/02* (2006.01)
*F16B 35/06* (2006.01)
*F16B 37/12* (2006.01)
*F16B 43/02* (2006.01)

(52) U.S. Cl.
CPC ............ *A61B 17/7049* (2013.01); *F16B 7/18* (2013.01); *F16B 33/02* (2013.01); *F16B 35/06* (2013.01); *F16B 37/125* (2013.01); *F16B 43/02* (2013.01)

(56) References Cited

U.S. PATENT DOCUMENTS

| | | |
|---|---|---|
| 2,268,576 A | 1/1942 | Drewett |
| 2,514,589 A | 7/1950 | Penman |
| 2,684,168 A | 7/1954 | McGinnis et al. |
| 2,783,809 A | 3/1957 | Haines et al. |
| 3,949,769 A | 4/1976 | Minka |
| 4,041,939 A | 8/1977 | Hall |
| 4,369,011 A | 1/1983 | Ploss |
| 4,601,491 A | 7/1986 | Bell et al. |
| 4,688,832 A | 8/1987 | Ortloff et al. |
| 4,763,644 A | 8/1988 | Webb |
| 4,846,614 A | 7/1989 | Steinbock |
| 4,850,775 A | 7/1989 | Lee et al. |
| 5,005,562 A | 4/1991 | Cotrel |
| 5,092,635 A | 3/1992 | DeLange et al. |
| 5,129,900 A | 7/1992 | Asher et al. |
| 5,190,543 A | 3/1993 | Schläpfer |
| 5,217,497 A | 6/1993 | Mehdian |
| 5,474,555 A | 12/1995 | Puno et al. |
| 5,536,268 A | 7/1996 | Griss |
| 5,605,457 A | 2/1997 | Bailey et al. |
| 5,605,458 A | 2/1997 | Bailey et al. |
| 5,607,304 A | 3/1997 | Bailey et al. |
| 5,782,833 A | 7/1998 | Haider |
| 5,797,911 A * | 8/1998 | Sherman ............ A61B 17/7037 606/266 |
| 5,810,818 A | 9/1998 | Errico et al. |
| 5,817,094 A | 10/1998 | Errico et al. |
| 5,858,020 A | 1/1999 | Johnson et al. |
| 5,873,878 A | 2/1999 | Harms et al. |
| 5,891,145 A | 4/1999 | Morrison et al. |
| 6,063,090 A * | 5/2000 | Schlapfer ............ A61B 17/7041 606/270 |
| 6,074,391 A * | 6/2000 | Metz-Stavenhagen A61B 17/7032 606/278 |
| 6,183,472 B1 | 2/2001 | Lutz |
| 6,224,596 B1 | 5/2001 | Jackson |
| 6,224,598 B1 | 5/2001 | Jackson |
| 6,231,575 B1 | 5/2001 | Krag |
| 6,280,442 B1 * | 8/2001 | Barker ................ A61B 17/7037 606/256 |
| 6,296,642 B1 * | 10/2001 | Morrison ............ A61B 17/7032 606/300 |
| 6,315,564 B1 | 11/2001 | Levisman |
| 6,454,768 B1 | 9/2002 | Jackson |
| 6,485,220 B2 | 11/2002 | Hecht |
| 6,485,491 B1 | 11/2002 | Farris et al. |
| 6,488,681 B2 | 12/2002 | Martin et al. |
| 6,726,687 B2 | 4/2004 | Jackson |
| 6,730,089 B2 | 5/2004 | Jackson |
| 7,018,375 B2 | 3/2006 | Biedermann et al. |
| 8,123,784 B2 | 2/2012 | Biedermann et al. |
| 2004/0186473 A1 | 9/2004 | Cournoyer et al. |

FOREIGN PATENT DOCUMENTS

| | | |
|---|---|---|
| DE | 199 12 364 A1 | 10/2000 |
| EP | 0 614 649 A1 | 9/1994 |
| JP | 8 112291 | 5/1996 |
| SU | 371359 | 2/1973 |
| WO | WO 95/01132 A | 1/1995 |
| WO | WO 00/27297 | 5/2000 |

OTHER PUBLICATIONS

Title pages of the 26th Edition of the Machinery's Handbook and pp. 1706 and 1816-1818.
Title page of the 21st Edition of the Machinery's Handbook and pp. 1336-1339.
Title pages of the 22nd Edition of the Machinery's Handbook and pp. 1324-1327.
Title pages of the 22nd Edition of the Machinery's Handbook and p. 1206.
Title page of the 27th Edition of the Machinery's Handbook and pp. 1846-1850.
United States Court of Appeals for the Federal Circuit, Opening Brief for Lutz Biedermann and Jurgen Harms, dated Jan. 28, 2013 for Appeal No. 2013-1080 (U.S. Appl. No. 10/306,057), 59 pages.
United States Court of Appeals for the Federal Circuit, Brief for Appellee, dated Apr. 8, 2013 for Appeal No. 2013-1080 (U.S. Appl. No. 10/306,057), 36 pages.
United States Court of Appeals for the Federal Circuit, Reply Brief for Lutz Biedermann and Jurgen Harms, dated May 9, 2013 for Appeal No. 2013-1080 (U.S. Appl. No. 10/306,057), 23 pages.
United States Court of Appeals for the Federal Circuit, Decision, dated Oct. 18, 2013 for Appeal No. 2013-1080 (U.S. Appl. No. 10/306,057), 17 pages.
Information from Machinery's Handbook provided by Chris McCauley, editor of Machinery's Handbook on Feb. 24, 2014, 3 pages.
Office action for U.S. Appl. No. 13/483,792, dated Oct. 3, 2012, 7 pages.
Final Rejection for U.S. Appl. No. 13/483,792, dated Jul. 15, 2013, 5 pages.
Office action for U.S. Appl. No. 13/968,222, dated May 19, 2016, 6 pages.
Office action for U.S. Appl. No. 13/356,431, dated Feb. 15, 2013, 11 pages.
Office action for U.S. Appl. No. 10/799,143, dated Feb. 23, 2006, 11 pages.
Final Office action for U.S. Appl. No. 10/799,143, dated Oct. 20, 2006, 7 pages.
Office action for U.S. Appl. No. 10/799,143, dated Jul. 12, 2007, 9 pages.
Final Office action for U.S. Appl. No. 10/799,143, dated Apr. 3, 2008, 10 pages.
Office action for U.S. Appl. No. 10/799,143, dated Jan. 7, 2009, 9 pages.
Final Office action for U.S. Appl. No. 10/799,143, dated Nov. 12, 2009, 10 pages.
Office action for U.S. Appl. No. 10/799,143, dated Jun. 21, 2010, 10 pages.
Office action for U.S. Appl. No. 10/799,143, dated Feb. 16, 2011, 10 pages.
Walker, John R. *Machining Fundamentals—Fundamentals Basic to Industry*, 1981, pp. 179-186, The Goodheart-Willcox Co., Inc., South Holland, Illinois.
Lascoe et al. *Machineshop—Operations and Setups*, 1973, pp. 380, 386, and 388, 4th Edition, American Technical Society, Chicago.
Opinion, 05-1415, Mar. 20, 2007, U.S. Court of Appeals for the Federal Circuit, *Cross Medical Products, Inc.* v. *Medtronic Sofamor Danek, Inc. et al.*, 24 pages.
Information Disclosure Statement and Form PTO/SB/08A/B for U.S. Appl. No. 10/799,143 dated Apr. 20, 2007, 4 pages.

* cited by examiner

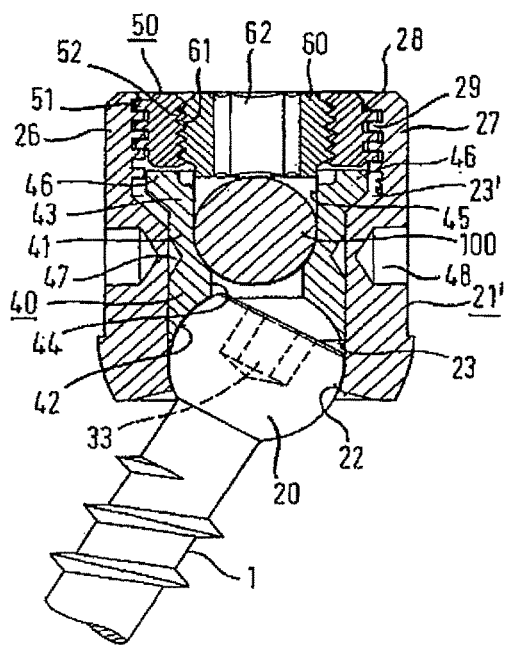
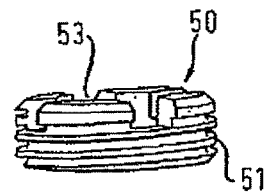
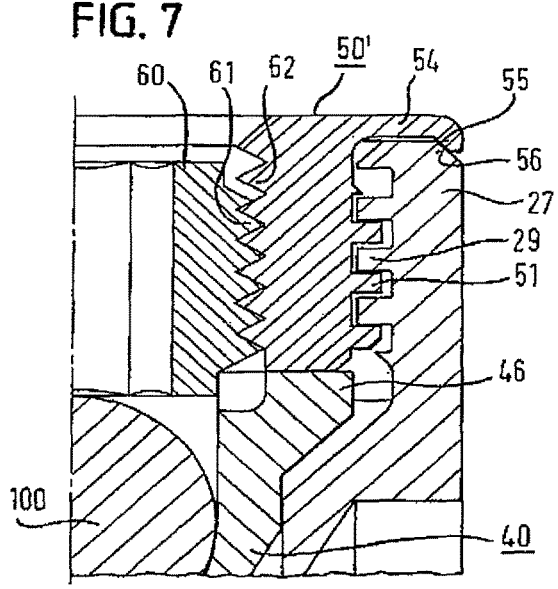
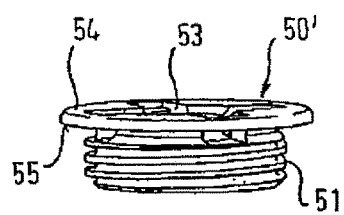

ELEMENT WITH A SHANK AND A HOLDING ELEMENT CONNECTED TO IT FOR CONNECTING TO A ROD

CROSS-REFERENCE TO RELATED APPLICATION(S)

This application is a continuation of U.S. patent application Ser. No. 14/327,434, filed Jul. 9, 2014, which is a continuation of U.S. patent application Ser. No. 10/306,057, filed Nov. 27, 2002, now U.S. Pat. No. 8,828,060, which claims priority of DE 101 57 969.1, filed Nov. 27, 2001, the entire disclosures of which are incorporated herein by reference.

The invention relates to an element to be used in spinal column surgery or accident surgery with a shank and a holding element connected to it for connecting to a rod.

A bone screw with a shank and a holding element connected to it for connecting to a rod according to the preamble of claim 1 is known from EP 0 614 649. In this so-called polyaxial bone screw described the inner thread of the open legs of the holding element or receiving part and the outer thread of the inner screw have substantially a rounded thread.

From U.S. Pat. No. 5,005,562 and U.S. Pat. No. 6,074,391 in each case an element according to the preamble of claim 1 is known. The inner thread of the open legs of the holding element or receiving part and the outer thread of the inner screw are constructed with a saw-tooth pitch to avoid splaying of the legs by radially acting forces during screwing in.

An element according to the preamble of claim 1 is also known from WO 00/27 297. In this element the flanks of the inner thread facing away from the open ends of the legs formed by the U-shaped recess enclose a negative angle with a plane perpendicular to the central axis of the receiving part. This is also intended to prevent splaying of the legs.

In the above-described devices either a device encircling the holding element from outside is required to prevent splaying of the legs or the thread to be used is difficult to produce.

This applies in particular to the thread known from WO 00/27 297 with the negative flank angle.

It is the object of the invention to provide an element with a shank and a holding element connected to it for connecting to a rod, which is easy to produce, compact in structure and easy to handle.

The object is achieved by an element according to claim 1. Further developments of the invention are cited in the subordinate claims.

The element according to the invention has the advantage that the inner thread of the legs or the outer thread of the locking element, constructed as a flat thread, is extremely easy to produce. This saves production costs and precision can be increased. As with this thread no forces act outwards in the radial direction, splaying of the open legs of the holding element is avoided and therefore no additional element to be applied from outside to avoid splaying is required. This enables a more compact structure.

Further features and advantages of the invention emerge from the description of embodiment examples using the figures.

FIG. 2b shows an enlarged illustration of a detail from FIG. 2a.

FIG. 3b shows an enlarged illustration of a detail from FIG. 3a.

FIG. 5 shows a sectional illustration of a third embodiment.

FIG. 6 shows a perspective view of the nut from FIG. 5.

FIG. 7 shows a partial view in section of a modification of the third embodiment.

FIG. 8 shows a perspective view of the nut of the embodiment from FIG. 7.

Figure 1:
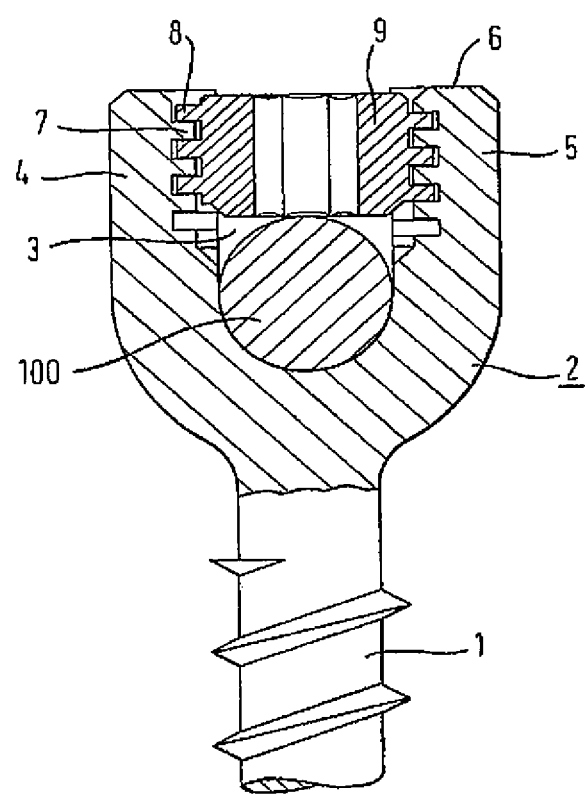
FIG. 1 shows a sectional illustration of a first embodiment of the element according to the invention.

The element according to the invention is constructed in the embodiment illustrated in FIG. 1 of the figures as a monoaxial bone screw. It has a shank 1 with a bone thread section and a receiving part 2, rigidly connected to it, for receiving a rod 100 connecting the bone screw to further bone screws. For this purpose the receiving part is provided with a recess 3 with a U-shaped cross-section, which is dimensioned just large enough for the rod 100 to be placed in it and fit into the bottom of the recess. By the U-shaped recess 3 two open legs 4, 5 are formed with in each case one open end 6 forming the upper edge of the receiving part 2. Adjacent to the open end 6 the legs 4, 5 have an inner thread 7, which cooperates with a corresponding outer thread 8 of an inner screw 9, to be screwed in between the legs 4, 5, to fix the rod 100.

As can be seen in particular in FIGS. 1 to 3b, the inner thread 7 and, corresponding to this, the outer thread 8 is constructed as a flat thread. This is characterised in that the thread flanks 7a, 7b of the inner thread enclose in each case an angle of 90° with the central axis M of the receiving part. Correspondingly, thread flanks 8a, 8b of the outer thread of the inner screw 9 enclose an angle of 90° with the screw axis S. The thread cross-section is substantially rectangular. The edges can further be constructed as rounded. The thread flanks are constructed without undercuts.

As emerges in particular from the enlarged illustration according to FIG. 2b and FIG. 3b, in this embodiment example the inner thread 7 of the legs and the outer thread 8 of the inner screw 9 are dimensioned relative to one another as follows: radius $r_1$ from the screw axis S to the root of the thread 8c of the inner screw 9 is smaller than radius $r_2$ from the central axis M of the receiving part 2 to its crest 7d. Radius $r_3$ from the screw axis S to the crest 8d of the inner screw 9 is smaller than radius $r_4$ from the central axis M of the receiving part 2 to the root of the thread 7c of its inner thread.

Figure 2A:
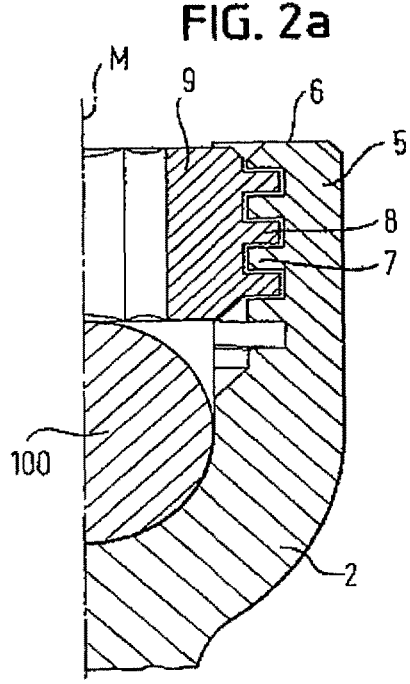
FIG. 2a shows a partial view of the embodiment of FIG. 1 with the inner screw not yet tightened.
Figure 2B:
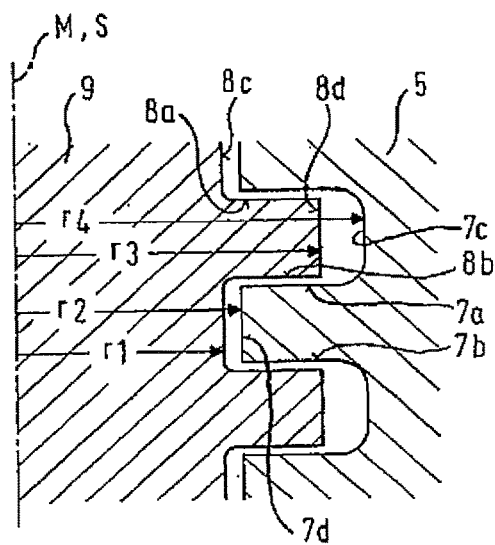
Figure 3A:
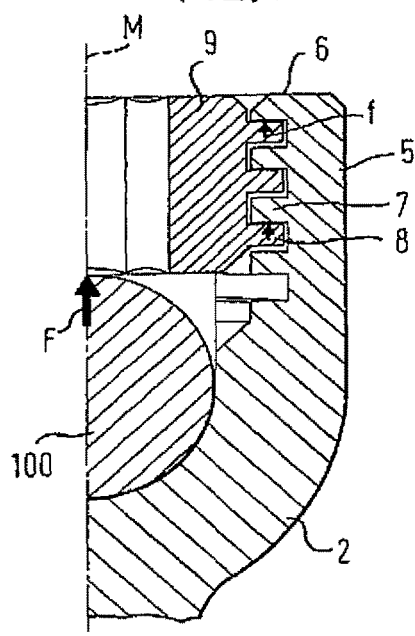
FIG. 3a shows a partial view of the embodiment of FIG. 1 with the inner screw tightened.
Figure 3B:
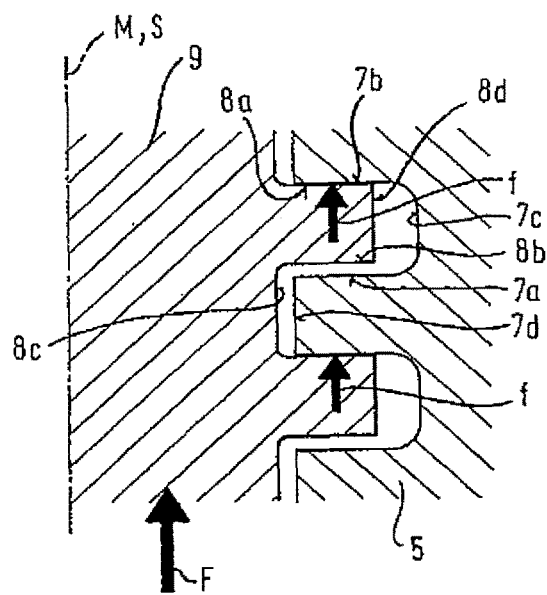

Furthermore, as shown in FIG. 2b, the dimensions of the thread are such that on unloaded bringing into engagement of inner screw and open legs 4, 5 of the receiving part there is a difference between radii $r_1$ and $r_2$, i.e. a radial play, of 1% to 5% of the outer diameter of the thread, preferably approximately 1%. In the axial direction there is, for a recess of approximately 5 mm, an axial play of approximately 10%.

In operation, after the rod has been placed into the receiving part 2, the inner screw 9 is first loosely screwed in, so that the rod can still be adjusted. To fix the rod 100, the inner screw 9 is tightened. It thereby experiences a counterforce, represented in FIGS. 3a and 3b by the arrow F. As a result flanks 8a of the outer thread facing the open end 6, and flanks 7b of the inner thread facing away from the open end come to be on top of one another. The force acting on the thread flanks therein acts only in the axial direction, as illustrated by the short arrows f in FIGS. 3a and 3b. Therefore there is no splaying of the legs 4, 5.

Figure 4:
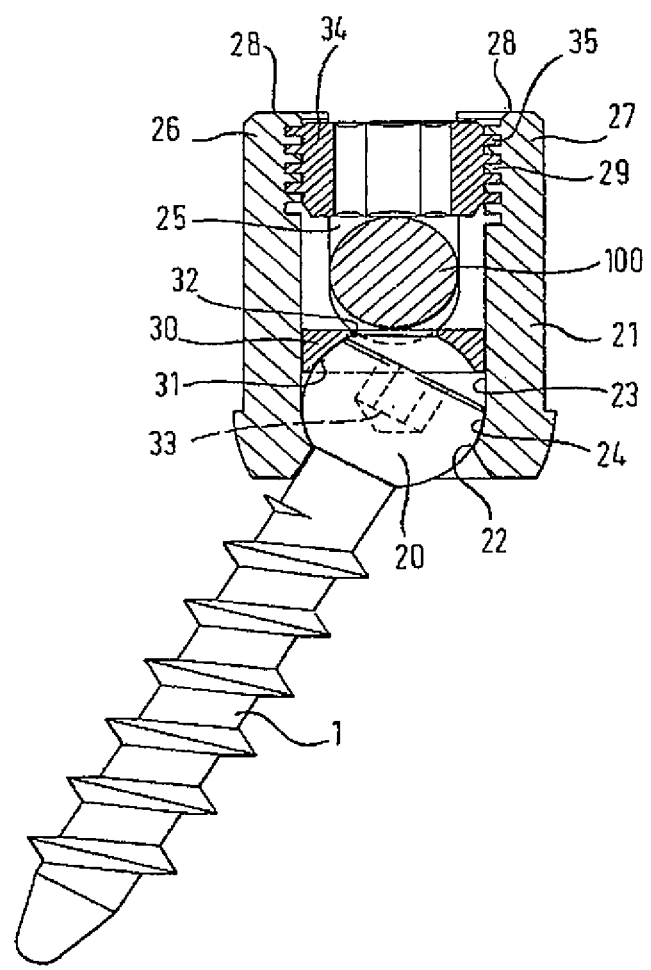
FIG. 4 shows a sectional illustration of a second embodiment.

In a second embodiment shown in FIG. 4 the element according to the invention is constructed as a polyaxial bone screw. The polyaxial bone screw has a screw element with a thread shank 1 with a bone thread which is connected to a receiving part 21 via a head 20, shaped like a segment of, a sphere. The receiving part 21 has on one of its ends a first bore 22, aligned symmetrically to the axis, the diameter of which is larger than that of the thread section of the shank 1 and smaller than that of the head 20. The receiving part 21 further has a coaxial second bore 23, which is open at the end opposite to the first bore 22 and the diameter of which is large enough for the screw element to be inserted through the open end with its thread section through the first bore 22 and with its head 20 as far as the bottom of the second bore 23. Between the first and the second bore a small coaxial section 24 is provided which is immediately adjacent to the first bore 22 and is constructed as spherical towards the open end, the radius being substantially identical to the section of the head 20 shaped like a segment of a sphere. Receiving part 21, like receiving part 2 of the first embodiment, has a U-shaped recess 25, arranged as symmetrical to the centre of the part, the bottom of which is directed towards the first bore 22 and by which two open legs 26, 27 are formed, the open end 28 of which forms the upper edge of the receiving part 21. In an area adjacent to the open end 28 the legs 26, 27 have an inner thread 29. The inner thread is constructed according to the invention as a flat thread, as described for the first embodiment.

Further provided is a pressure element 30, which is constructed in such a way that it has on its side facing the head 20 a spherical indentation 31, the radius of which is substantially identical to the radius of the section of the head 20 shaped like a segment of a sphere. The outer diameter of the pressure element is chosen in such a way that the pressure element can perform a sliding movement in the receiving part 21, in other words is displaceable towards the head 20. The pressure element further has a coaxial bore 32 for access to a recess 33 in the screw head 20 for bringing into engagement with a screwing in tool.

To fix the rod 100 and the head in its angle position an inner thread 34 is provided, similarly to in the first embodiment, which has an outer thread 35 cooperating with the inner thread 29 of the legs. The outer thread is again constructed as a flat thread, as in the first embodiment.

In operation the screw element is screwed into the bone after being placed in the receiving part 21. The pressure element 30 and the rod 100 are then inserted in turn. At this stage the screw head 20 is still swivellable. By screwing in the inner thread 34 the screw element and the receiving part 21 are fixed to one another and therefore also the rod 100. As, owing to the construction of the cooperating thread of the legs and the inner screw as flat thread no splaying of the legs takes place, no additional securing is required, whereby the polyaxial screw can be configured compactly and produced at a reasonable price.

The third embodiment illustrated in FIGS. 5 and 6 also shows a polyaxial bone screw. Parts corresponding to the second embodiment are provided with the same reference numerals. The third embodiment differs from the second embodiment in the construction of the receiving part, the pressure element and the inner screw.

The receiving part 21' has, adjacent to its open end 28, a section 23' which has a larger diameter than the second bore and which tapers conically towards the first bore. The construction of the receiving part in respect of the U-shaped recess and the legs 26, 27 is as in the second embodiment. Adjacent to the open end 28 the inner thread 29 is formed in a predetermined area in section 23'. The inner thread is constructed, as in the first and second embodiment, as a flat thread.

The pressure element 40 of this embodiment has a substantially cylindrical first section 41, the outer diameter of which is chosen in such a way that the pressure element can slide in the second bore 23 of the receiving part 21'. In this first section 41 a recess 42, shaped like the segment of a sphere and widening towards the end, is provided, the sphere radius of which is chosen in such a way that in a state inserted into the receiving part it partially encircles the head 20 of the screw element. At the opposite end the pressure element 40 is formed in a second section 43 with an outer diameter enlarged compared with the diameter of the first section 41, which is larger than the inner diameter of the bore 23 of the receiving part 21' but smaller than the inner diameter between the legs 26, 27. The second section 43, corresponding to the construction of the receiving part, verges conically into the first section 41. The pressure element 40 further has a central bore 44 extending therethrough. The diameter of the central bore 44 is dimensioned as just large enough for a screw tool to be guided through it for bringing into engagement with the recess 33 provided in the head 20.

A substantial difference from the pressure element of the second embodiment is that the pressure element of the third embodiment is lengthened in the direction of the open end 28 of the legs. For this purpose it has at its end opposite the recess 42 shaped like the segment of a sphere a U-shaped recess 45, wherein the dimensions of the U-shaped recess of the pressure element are such that the rod 100 can be placed in the channel formed thereby. The depth of the U-shaped recess 45, seen in the direction of the cylindrical axis of the receiving part 21', is larger than the diameter of the rod 100 to be received such that the pressure element 40 projects upwards above the rod 100 with lateral legs 46.

The pressure element 40 further has on its outer casing two countersunk bores 47, arranged opposite and offset by 90° from the centre of the U-shaped recess and extending in the radial direction, which cooperate with corresponding crimped bores 48 in the outer casing of the receiving part 21'.

Instead of the inner screw 9 of the first and second embodiment, in the third embodiment a nut 50, which can be screwed in between the legs 26, 27 of the receiving part, is provided with an outer thread 51, which cooperates with the inner thread 29 of the legs. The outer thread 51 of the nut is constructed as a flat thread, like that of the inner thread of the previous embodiments. The inner thread 52 of the nut 50 is a metric thread. As can be seen from FIG. 6, the nut has on one of its ends slits 53 for bringing into engagement with a screw tool.

Further provided is an inner screw or clamping or set screw 60 for screwing into the nut 50, which has a metric outer thread 61 which cooperates with the inner thread 52 of the nut 50. The inner screw 60 has a recess 62 for bringing into engagement with a screw tool.

In operation, as in the second embodiment, first the screw element is put into the receiving part. Then, differently from the second embodiment, the pressure element 40 is inserted and is first held loosely over the countersunk and crimped bores 47, 48. Following this the bone screw is screwed into the bone and the rod 100 then placed in Thereupon the nut 50 is screwed in, with inner screw 60 at first loosely screwed into it, until the nut impacts on the upper end of the legs 46 and therefore the pressure element 40 presses on the screw head 20, so that it is locked in its position in the receiving part. Owing to the construction of the inner thread 29 of the legs and the outer thread of the nut 50 as flat threads, the nut 50 does not experience any radial force component, but only an axially directed force, which is why no splaying of the legs takes place. The screw head is thus securely locked. Because the legs 46 of the pressure element project above the placed in rod 100, the rod is still displaceable and yet prevented by the nut 50 from falling out or tilting. Finally, the inner screw 60 is tightened until it presses on the rod 100 and fixes it. Fixing the rod thus takes place independently of fixing the head.

In the third embodiment shown in FIGS. 5 and 6 the nut 50 and the inner screw 60 are fully screwed into the receiving part 21'. In the modified embodiment shown in FIGS. 7 and 8 the nut 50' has at the end containing the slits 53 a ring-shaped projection 54, the outer diameter of which corresponds to the outer diameter of the receiving part 21'. The open end of the ring-shaped projection 54 is further constructed like a cap and has an inclined face 55 which, in the state screwed into the receiving part 21', cooperates with a corresponding bevelled face 56 at the open end 28 of the receiving part 21'. The length of the nut 50' in the axial direction is chosen in such a way that in the state fully screwed into the receiving part 21' the nut 50' presses on the pressure element 40 with a predetermined force, the ring-shaped projection 54 acting as a stop to limit this force.

Operation takes place as in the third embodiment with the single difference that the nut 50' can be screwed in only until it rests against the ring-shaped projection 54 and thus the force acting on the pressure element is set to a predetermined value.

To prevent deformation of the legs 26, 27 of the receiving part 21' by axial wringing caused by torsion forces at the moment of tightening, the cap-like projection 54 with its bevelled face 55 grips on to the corresponding bevelled face on the outer face of the receiving part. After final tightening there is no longer any torsional loading of this kind and the legs 26, 27 do not experience any force acting outwards, which could occasion loosening of the nut 50'.

Alternatively to the cap-like construction of the projection 54, a ring provided on the screwing in tool can be used.

In a modification of the above-described embodiments a hook is provided instead of the thread shank 1. In a further modification of the polyaxial embodiments, instead of the thread shank 1 or the hook, a bar or a rod-shaped element is provided, which has a head shaped like a segment of a sphere on both ends and is connected to a receiving part of the kind described. In this way an element of this kind can be used as connecting element between two rods 100.

What is claimed is:

1. A polyaxial bone anchor comprising:
an anchor element having a shank and a head, the head having a spherically shaped segment;
a receiving part having a recess in a top end having a U-shaped cross-section forming two legs for receiving a rod therebetween, the receiving part comprising an inner thread on each of the two legs;
a locking element to lock the rod in the recess of the receiving part, wherein the locking element has a central axis, a first end with a flat annular surface that extends radially relative to the central axis in a first plane to engage the rod when the locking element is threaded to the receiving part, and a second end with a flat annular surface that extends radially relative to the central axis in a second plane that is parallel to the first plane; and
a pressure element that cooperates with the head to fix an angular position of the anchor element relative to the receiving part when the locking element is tightened;
wherein the receiving part and the head of the anchor element are configured to form a polyaxial connection that permits the spherically shaped segment of the head to swivel in the receiving part when unlocked and wherein tightening of the locking element fixes the angular position of the anchor element relative to the receiving part;
wherein the locking element comprises an outer thread having two flanks, the outer thread cooperates with, the inner thread of the two legs, an upper flank of the two flanks of the outer thread facing the top end of the receiving part and a lower flank of the two flanks of the outer thread facing away from the top end of the receiving part when the locking element is assembled to the receiving part;
wherein in a cross-section of the outer thread of the locking element, the upper and lower flanks of the outer thread are symmetrical and each flank encloses an angle of 90 degrees with the central axis of the locking element;
wherein the inner thread on each of the two legs comprises two flanks, an upper flank facing the top end of the receiving part and a lower flank facing away from the top end of the receiving part; and
wherein a cross-section of the outer thread of the locking element is substantially rectangular and when assembled the lower flank of the inner thread matches a shape of the upper flank of the outer thread such that locking the rod between the legs with the locking element avoids splaying of the legs.

2. The polyaxial bone anchor of claim 1, wherein, in a view of the U-shaped cross-section of the receiving part when the locking element is assembled to the receiving part, the outer thread of the locking element comprises a maximum of four fully formed thread sections.

3. The polyaxial bone anchor of claim 1, wherein the central axis of the locking element defines a rotational axis of the locking element, with the first and second ends spaced from each other along the rotational axis, and wherein the locking element has an opening at each of the first and second ends, the respective openings at the first and second ends having the same cross-section, such that the opening at each of the first and second ends of the locking element is configured to receive a screw tool to tighten the locking element against the rod.

4. The polyaxial bone anchor of claim 3, wherein a single recess passes through the entire length of the locking element and intersects the first and second ends to define the openings at the first and second ends.

5. The polyaxial bone anchor of claim 3, wherein the locking element is configured to be threaded to the receiving part from either end of the locking element.

6. The polyaxial bone anchor of claim 1, wherein the locking element comprises a nut having an inner thread and an inner screw that cooperates with the inner thread of the nut.

7. The polyaxial bone anchor of claim 6, further comprising the rod, wherein, when the pressure element is assembled to the receiving part, the pressure element comprises a side facing away from the head, the side having a recess which is open to the top end for receiving the rod, the recess having an axial depth in an axial direction larger than a diameter of the rod.

8. The polyaxial bone anchor of claim 1, wherein the locking element fits entirely between the legs of the receiving part.

9. The polyaxial bone anchor of claim 1, wherein a cross-section of the inner thread on each of the two legs of the receiving part is substantially rectangular.

10. The polyaxial bone anchor of claim 9, wherein the two flanks of the inner thread on each of the two legs are without undercuts or steps.

11. The polyaxial bone anchor of claim 1, wherein the receiving part comprises an unthreaded bore adjacent to and below the inner thread on each of the two legs, the unthreaded bore having a diameter greater than a diameter at the crest of the inner thread, wherein the U-shaped cross-section has a bottom opposite the top end of the receiving part, and wherein the unthreaded bore is positioned closer axially to a bottommost crest of the inner thread than to the bottom of the U-shaped cross-section.

12. The polyaxial bone anchor of claim 1, wherein the pressure element has a coaxial bore to provide access to the head of the anchor element when assembled.

13. The polyaxial bone anchor of claim 1, wherein the receiving part has a seat and, when assembled, the spherically shaped segment of the head directly contacts and is permitted to swivel on the seat prior to locking.

14. A polyaxial bone anchor comprising:
an anchor element having a shank and a head, the head having a spherically shaped segment;
a rod;
a receiving part having a recess in a tap end having a U-shaped cross-section forming two legs for receiving the rod therebetween, the receiving part comprising an inner thread on each of the two legs;
a two part locking element to lock the rod in the recess of the receiving part, the two part locking element comprising an outer locking element and an inner locking element; and
a pressure element that cooperates with the head to fix an angular position of the anchor element relative to the receiving part when the outer or inner locking element is tightened, wherein when the anchor element and the pressure element are assembled to the receiving part, a side of the pressure element facing away from the head has a recess that is open to the top end for receiving the rod, such that when the rod is received in the recess of the pressure element the outer locking element is configured to contact the pressure element and the inner locking element is configured to contact the rod;
wherein the receiving part and the head of the anchor element are configured to form a polyaxial connection that permits the spherically shaped segment of the head to swivel in the receiving part when unlocked and wherein tightening of the outer or inner locking element fixes the angular position of the anchor element relative to the receiving part;
wherein the outer locking element comprises an outer thread having two flanks, the outer thread cooperates with the inner thread of the two legs, an upper flank of the two flanks of the outer thread facing the top end of the receiving part and a lower flank of the two flanks of the outer thread facing away from the top end of the receiving part when the outer locking element is assembled to the receiving part;

wherein in a cross-section of the outer thread of the outer locking element, the upper and lower flanks of the outer thread are symmetrical and each flank encloses an angle of 90 degrees with a central axis of the outer locking element;
wherein the inner thread on each of the two legs comprises two flanks, an upper flank facing the top end of the receiving part and a lower flank facing away from the top end of the receiving part;
wherein a cross-section of the outer thread of the outer locking element is substantially rectangular, and when assembled, the lower flank of the inner thread matches a shape of the upper flank of the outer thread such that locking the rod between the legs with the outer or inner locking element avoids splaying of the legs; and
wherein the inner locking element has an outer thread that cooperates with an inner thread of the outer locking element to permit movement of the inner locking element into the recess of the receiving part to lock the rod between the two legs.

15. The polyaxial bone anchor of claim 14, wherein, in a view of the U-shaped cross-section of the receiving part when the outer locking element is assembled to the receiving part, the outer thread of the outer locking element comprises a maximum of four fully formed thread sections.

16. The polyaxial bone anchor of claim 14, wherein the outer locking element has tool engagement grooves extending longitudinally along the inside of the outer locking element for engagement with a locking tool.

17. The polyaxial bone anchor of claim 16, wherein respective upper ends of the tool engagement grooves are spaced from an outer surface of the outer locking element by a solid annular wall of the outer locking element.

18. The polyaxial bone anchor of claim 14, wherein the recess of the pressure element has a depth in an axial direction that is larger than a diameter of the rod.

19. The polyaxial bone anchor of claim 14, wherein the outer locking element fits entirely between the legs of the receiving part.

20. The polyaxial bone anchor of claim 14, wherein the outer locking element has a first end with a flat annular surface that extends radially relative to the central axis in a first plane to engage the rod when the outer locking element is threaded to the receiving part, and a second end with a flat annular surface that extends radially relative to the central axis in a second plane that is parallel to the first plane.

21. The polyaxial bone anchor of claim 14, wherein a cross-section of the inner thread on each of the two legs of the receiving part is substantially rectangular.

22. The polyaxial bone anchor of claim 21, wherein the two flanks of the inner thread on each of the two legs are without undercuts or steps.

23. The polyaxial bone anchor of claim 14, wherein the receiving part comprises an unthreaded bore adjacent to and below the inner thread on each of the two legs, the unthreaded bore having a diameter greater than a diameter at the crest of the inner thread, wherein the U-shaped cross-section has a bottom opposite the top end of the receiving part, and wherein the unthreaded bore is positioned closer axially to a bottommost crest of the inner thread than to the bottom of the U-shaped cross-section.

24. The polyaxial bone anchor of claim 14, wherein the pressure element has a coaxial bore to provide access to the head of the anchor element when assembled.

25. A method of connecting a rod to a bone with a polyaxial bone anchor, wherein the polyaxial bone anchor comprises:

an anchor element having a shank and a head, the head having a spherically shaped segment;

a receiving part having a recess in a top end having a U-shaped cross-section forming two legs for receiving the rod therebetween, the receiving part comprising an inner thread on each of the two legs;

a locking element to lock the rod in the recess of the receiving part, wherein the locking element has a central axis, a first end with a flat annular surface that extends radially relative to the central axis in a first plane to engage the rod when the locking element is threaded to the receiving part, and a second end with a flat annular surface that extends radially relative to the central axis in a second plane that is parallel to the first plane; and a pressure element that cooperates with the head to fix an angular position of the anchor element relative to the receiving part when the locking element is tightened;

wherein the receiving part and the head of the anchor element are configured to form a polyaxial connection that permits the spherically shaped segment of the head to swivel in the receiving part when unlocked and wherein tightening of the locking element fixes the angular position of the anchor element relative to the receiving part;

wherein the locking element comprises an outer thread having two flanks, the outer thread cooperates with the inner thread of the two legs, an upper flank of the two flanks of the outer thread facing the top end of the receiving part and a lower flank of the two flanks of the outer thread facing away from the top end of the receiving part when the locking element is assembled to the receiving part;

wherein in a cross-section of the outer thread of the locking element, the upper and lower flanks of the outer thread are symmetrical and each flank encloses an angle of 90 degrees with the central axis of the locking element;

wherein the inner thread on each of the two legs comprises two flanks, an upper flank facing the top end of the receiving part and a lower flank facing away from the top end of the receiving part; and wherein a cross-section of the outer thread of the locking element is substantially rectangular, and when assembled, the lower flank of the inner thread matches a shape of the upper flank of the outer thread such that locking the rod between the legs with the locking element avoids splaying of the legs, the method comprising:

attaching the shank to a bone;

placing the rod into the recess of the receiving part;

threading the locking element to the inner threads of the legs of the receiving part; and sufficiently tightening the locking element to lock the rod in the receiving part and to fix the angular position of the anchor element relative to the receiving part while avoiding splaying of the legs.

26. A polyaxial bone anchor comprising:

an anchor element having a shank and a head, the head having a spherically shaped segment;

a receiving part having a recess in a top end having a U-shaped cross-section forming two legs for receiving a rod therebetween, the receiving part comprising an inner thread on each of the two legs;

a locking element to lock the rod in the recess of the receiving part, wherein the locking element has a central axis defining a rotational axis of the locking element and first and second ends spaced from each other along the rotational axis; and a pressure element that cooperates with the head to fix an angular position of the anchor element relative to the receiving part when the locking element is tightened;

wherein the receiving part and the head of the anchor element are configured to form a polyaxial connection that permits the spherically shaped segment of the head to swivel in the receiving part when unlocked and wherein tightening of the locking element fixes the angular position of the anchor element relative to the receiving part;

wherein the locking element comprises an outer thread having two flanks, the outer thread cooperates with the inner thread of the two legs, an upper flank of the two flanks of the outer thread facing the top end of the receiving part and a lower flank of the two flanks of the outer thread facing away from the top end of the receiving part when the locking element is assembled to the receiving part;

wherein in a cross-section of the outer thread of the locking element, the upper and lower flanks of the outer thread are symmetrical and each flank encloses an angle of 90 degrees with the central axis of the locking element, and wherein the locking element has an opening at each of the first and second ends, the respective openings at the first and second ends having the same cross-section, such that the opening at each of the first and second ends of the locking element is configured to receive a screw tool for threading the locking element to the receiving part from either end of the locking element and for tightening the locking element against the rod;

wherein the inner thread on each of the two legs comprises two flanks, an upper flank facing the top end of the receiving part and a lower flank facing away from the top end of the receiving part; and wherein a cross-section of the outer thread of the locking element is substantially rectangular, and when assembled, the lower flank of the inner thread matches a shape of the upper flank of the outer thread such that locking the rod between the legs with the locking element avoids splaying of the legs.

27. The polyaxial bone anchor of claim 26, wherein, in a view of the U-shaped cross-section of the receiving part when the locking element is assembled to the receiving part, the outer thread of the locking element comprises a maximum of four fully formed thread sections.

28. The polyaxial bone anchor of claim 26, wherein a single recess passes through the entire length of the locking element and intersects the first and second ends to define the openings at the first and second ends.

29. The polyaxial bone anchor of claim 26, wherein the locking element fits entirely between the legs of the receiving part.

30. The polyaxial bone anchor of claim 26, wherein a cross-section of the inner thread on each of the two legs of the receiving part is substantially rectangular.

31. The polyaxial bone anchor of claim 30, wherein the two flanks of the inner thread on each of the two legs are without undercuts or steps.

32. The polyaxial bone anchor of claim 26, wherein the receiving part comprises an unthreaded bore adjacent to and below the inner thread on each of the two legs, the unthreaded bore having a diameter greater than a diameter at the crest of the inner thread, wherein the U-shaped cross-section has a bottom opposite the top end of the receiving part, and wherein the unthreaded bore is positioned closer axially to a bottommost crest of the inner thread than to the bottom of the U-shaped cross-section.

33. The polyaxial bone anchor of claim 26, wherein the pressure element has a coaxial bore to provide access to the head of the anchor element when assembled.

34. The polyaxial bone anchor of claim 26, wherein the receiving part has a seat and, when assembled, the spherically shaped segment of the head directly contacts and is permitted to swivel on the seat prior to locking.

35. A polyaxial bone anchor comprising:
   an anchor element having a shank and a head, the head having a spherically shaped segment;
   a receiving part having a recess in a top end having a U-shaped cross-section forming two legs for receiving a rod therebetween, the U-shaped cross-section having a bottom opposite the top end, the receiving part comprising an inner thread on each of the two legs and an unthreaded bore adjacent to and below the inner thread on each of the two legs, the unthreaded bore having a diameter greater than a diameter at the crest of the inner thread, wherein the unthreaded bore is positioned closer axially to a bottommost crest of the inner thread than to the bottom of the U-shaped cross-section;
   a locking element to lock the rod in the recess of the receiving part; and
   a pressure element that cooperates with the head to fix an angular position of the anchor element relative to the receiving part when the locking element is tightened;
   wherein the receiving part and the head of the anchor element are configured to form a polyaxial connection that permits the spherically shaped segment of the head to swivel in the receiving part when unlocked and wherein tightening of the locking element fixes the angular position of the anchor element relative to the receiving part;
   wherein the locking element comprises an outer thread having two flanks, the outer thread cooperates with the inner thread of the two legs, an upper flank of the two flanks of the outer thread facing the top end of the receiving part and a lower flank of the two flanks of the outer thread facing away from the top end of the receiving part when the locking element is assembled to the receiving part;
   wherein in a cross-section of the outer thread of the locking element, the upper and lower flanks of the outer thread are symmetrical and each flank encloses an angle of 90 degrees with a central axis of the locking element;
   wherein the inner thread on each of the two legs comprises two flanks, an upper flank facing the top end of the receiving part and a lower flank facing away from the top end of the receiving part; and
   wherein a cross-section of the outer thread of the locking element is substantially rectangular, and when assembled, the lower flank of the inner thread matches a shape of the upper flank of the outer thread such that locking the rod between the legs with the locking element avoids splaying of the legs.

* * * * *

UNITED STATES PATENT AND TRADEMARK OFFICE
CERTIFICATE OF CORRECTION

PATENT NO. : 9,895,173 B2  
APPLICATION NO. : 15/094784  
DATED : February 20, 2018  
INVENTOR(S) : Lutz Biedermann et al.

Page 1 of 1

It is certified that error appears in the above-identified patent and that said Letters Patent is hereby corrected as shown below:

In the Specification

Column 3, Line 66, after "second bore" insert -- 23 --

Column 5, Line 38, after Second Occurrence "face" insert -- 56 --

In the Claims

Column 6, Line 16, Claim 1, delete "with," and insert -- with --

Column 6, Line 33, Claim 1, delete "rectangular" and insert -- rectangular, --

Column 6, Line 34, Claim 1, delete "assembled" and insert -- assembled, --

Column 7, Line 34, Claim 14, delete "tap" and insert -- top --

Column 7, Line 50, Claim 14, First Occurrence delete "element" and insert -- element, --

Signed and Sealed this  
Fourteenth Day of May, 2019

Andrei Iancu  
*Director of the United States Patent and Trademark Office*